United States Patent
Fein et al.

[11] Patent Number: 6,016,372
[45] Date of Patent: Jan. 18, 2000

[54] CHEMICAL SENSING TECHNIQUES EMPLOYING LIQUID-CORE OPTICAL FIBERS

[75] Inventors: Harry Fein, Venice; Su-Yi Liu, Sarasota, both of Fla.

[73] Assignee: World Precision Instruments, Inc., Sarasota, Fla.

[21] Appl. No.: 09/055,865

[22] Filed: Apr. 6, 1998

Related U.S. Application Data

[63] Continuation-in-part of application No. 08/951,254, Oct. 16, 1997.

[51] Int. Cl.⁷ ...................................... G02B 6/20
[52] U.S. Cl. ...................... 385/12; 385/125; 250/227.18
[58] Field of Search ........................... 385/12, 125, 123; 250/227.14, 227.18, 459.1, 461.2, 473.1, 474.1; 356/301, 133, 436

[56] References Cited

U.S. PATENT DOCUMENTS 5,444,807  8/1995  Liu .......................................... 385/125

OTHER PUBLICATIONS

"Liquid–Core Waveguides for Chemical Sensing", SPIE vol. 2293, pp. 71–79, 1994.

Primary Examiner—John D. Lee
Assistant Examiner—Victoria D. Hao
Attorney, Agent, or Firm—Alix, Yale & Ristas, LLP

[57] ABSTRACT

A gas or vapor permeable optical fiber waveguide with a liquid core is employed as a probe for the detection or measurement of a chemical specie of interest by filling the waveguide core region with a reagent liquid which undergoes a change in an optical characteristic thereof when exposed to the chemical specie and then inserting the filled waveguide into an environment in which the chemical specie may be present. The chemical specie, if present, will permeate through the waveguide wall and react with or be absorbed in the core liquid. Sensitivity is enhanced by controlling the pressure differential across the waveguide wall and/or by shaping the waveguide to enlarge the surface area. When the reaction generates light, the devices which detect that light will be shaped and disposed to maximize the collection thereof.

21 Claims, 4 Drawing Sheets

CHEMICAL SENSING TECHNIQUES EMPLOYING LIQUID-CORE OPTICAL FIBERS

CROSS-REFERENCE TO RELATED APPLICATION

This application is a continuation-in-part of application Ser. No. 08/951,254 filed Oct. 16, 1997 and entitled CHEMICAL SENSING TECHNIQUES EMPLOYING LIQUID-CORE OPTICAL FIBERS.

BACKGROUND OF THE INVENTION

1. Field of the Invention

This invention relates to improvements in the optical detection of different chemical species and, particularly, to enhancing the efficiency of techniques for identification and/or quantitative measurement of chemical substances of interest wherein changes in the optical properties of a reagent/solvent caused by the reaction with or dissolution of the said chemical substance in the reagent/solvent are detected. More specifically, the present invention is directed to devices for use in optically detecting the presence and/or concentration of species which are in the gas or vapor phase or are dissolved in a liquid matrix and, especially, to apparatus which enables the sensing of changes in the optical properties of a confined light conducting medium resulting from exposure of the confining vessel to the sample matrix of interest. Accordingly, the general objects of the present invention are to provide novel and improved techniques and apparatus of such character.

2. Description of the Prior Art

The use of fiber optics in chemical analysis is known in the art. In the prior art, there are two main classes of fiber optic based sensors employed in such analysis. In a first type of prior art sensor, a relatively long length of solid optical fiber is employed as the sensing element and analysis light passed through the fiber interacts with the medium surrounding the fiber. This interaction occurs because the light used to internally illuminate the fiber, i.e., the analysis light, penetrates the external medium to a distance equivalent to ¼ of its wavelength, i.e., to a distance much less than the radius of the fiber. Such sensors are called evanescent wave sensors. The main disadvantage incident to the use of evanescent sensors is limited sensitivity. (See for example, "Fiber Optic Optrodes for Chemical Sensing", Brenci and Baldini, in Proceedings, 8th International Conference on Optical Fiber Sensors, pages 313–319, 1992; and "Fiber-Optic pH Sensor Based on Evanescent Wave Absorption Spectroscopy", Ge et al, Analytical Chemistry, volume 65, pages 2335–2338, 1993.)

In the second type of prior art fiber optic based chemical sensor, which has found more practical applications when compared to the above-mentioned type device, light launched into the proximal end of an optical fiber emerges at the distal end thereof to interact with a "target" substrate or solution that is affected by the chemical composition of the medium in which the target is present. The light interaction can be probed by observing changes in either light absorption or the light emission properties of the target substrate/solution. In a fluorometric mode of operation, a light beam of a wavelength suitable to excite fluorescence is launched through the fiber and the emitted fluorescent light is collected by, for example, the same fiber and separated by a suitable optical arrangement such as a dichroic mirror. (See, e.g., "Enzyme-based Fiber Optic Zinc Biosensor", Thompson and Jones, Analytical Chemistry, volume 65, pages 730–734, 1993); and "Fiber Optic pH Sensor Based on Phase Fluorescence Lifetime", Thompson and Lakowicz, Analytical Chemistry, volume 65, pages 853–856, 1993). Alternatively, the emitted fluorescent light can be collected by a second fiber(s). (See, e.g., "Novel Techniques and Materials for Fiber Optic Chemical Sensing", Wolfbeis, in Optical Fiber Sensors, Springer Proceedings in Physics, Volume 44, pages 416–424, 1989).

Absorptiometric measurements employing this second type of sensor typically implement a bifurcated collection technique, i.e., a second fiber(s) is used to receive the light to be analyzed. Most commonly, in absorption-type sensors, a reflecting optical target containing an immobilized reagent capable of undergoing a spectral change upon interaction with an analyte of interest in the surrounding medium is located at the fiber tip. Light (monochromatic or broadband) launched through the fiber is reflected off this target and single or multiwavelength measurements are made on the reflected light. (See, e.g., "Potentiometric and Fiber Optic Sensors for pH Based on an Electropolymerized Cobalt Porphyrin"), Blair et al, Analytical Chemistry, volume 65, pages 2155–2158, 1993; "Fiber Optic Sensors for pH and Carbon Dioxide Using a Self Referencing Dye", Parker et al, Analytical Chemistry, volume 65, pages 2329–2334, 1993; and "Current Developments in Optical Biochemical Sensors", Narayanaswamy, Biosensors and Bioelectronics, Volume 6, pages 467–475, 1991). Such immobilized reagents can also be used for fluorescence measurements. (See, e.g., "Fluorocarbon-based Immobilization of a Fluoroionophore for Preparation of Fiber Optic Sensors", Blair et al, Analytical Chemistry, volume 65, pages 945–947.)

The employment of an immobilized reagent, while attractive in theory, generally results in a sensor with a severely limited life expectancy due to reagent loss from photodecomposition or leaching. To solve this problem, resort has been had to renewing the reagent and, particularly, to flowing the reagent through the sensor probe. (See, e.g., "Measurement of Seawater $pCO_2$ Using a Renewable—Reagent Fiber Optic Sensor with Colorimetric Detection", DeGrandpre, Analytical Chemistry, volume 65, pages 331–337, 1993). In the extant art embodying such flow-through sensors, the tip of the optical fiber is typically located at a first end of a cylindrical chamber, and a reflector is disposed at the opposite end of the chamber. Provision is made for the continuous introduction of a suitable reagent and its withdrawal via conduits which are in fluid communication with the chamber and, typically, oriented in parallel with the optical fiber. The chamber will in part be permeable to the analyte of interest. The analyte thus permeates through a chamber wall and reacts with the reagent thereby producing a change that can be optically monitored. The rate of reagent flow governs the attainable sensitivity, i.e., sensitivity increases with decreasing flow, while response time decreases with increasing flow. In the reflectance mode, as described above, the effective path length is twice the distance between the fiber tip and the oppositely disposed reflector. The sensor can also be configured with a transmitting fiber at one end of the chamber and an oppositely disposed receiving fiber whereby the path length essentially becomes the length of the chamber. In either case, limited pathlengths are generally attainable, due to severe light loss, and maximum achievable sensitivity is very limited.

Collection of analytes into a reagent flowing through a permeable membrane is well known in the art. The collected analyte is typically measured colorimetrically or fluorometrically in a system external and separate from the collector with or without further reagent addition and reaction.

If a sufficient membrane area is provided for analyte collection, parts per trillion levels of analytes can be detected in favorable cases. (See, e.g., "Determination of Gaseous Hydrogen Peroxide at Parts per Trillion Levels with a Nafion membrane Diffusion Scrubber and a Single-Line Flow-injection System", Dasgupta et al, Analytica Chimica Acta, Volume 260, pages 57–64, 1992; and "Measurement of Atmospheric Ammonia", Dasgupta et al, Environmental Science and Technology, Volume 23, pages 1467–1474, 1989). The sensitivity of a renewable-reagent fiber optic sensor employing this mode of analyte collection would be expected by those skilled in the art to be very low because the length of the membrane that can be used is constrained by the light loss through the membrane.

A renewable reagent liquid core waveguide chemical sensor which uses a membrane material as both the sampling and waveguiding component has been reported. (See, e.g., "Liquid Core Waveguides for Chemical Sensing", Hong and Burgess, Proceedings SPIE, Vol. 2293, pgs. 71–79, 1994). This paper proposes a liquid core waveguide comprised of then available permeable polymers, i.e., PTFE and FEP. Such waveguides, however, have very limited utility because their refractive indexes are greater than that of water, i.e., exceed 1.33, and because they are not optically clear and thus can conduct light for only a short distance. Further, while being somewhat permeable to gases, such polymers do not have sufficient permeability to function as a sensor probe with significant commercial applicability. In the use of such waveguides, it is necessary to incorporate ethylene glycol or some other non-aqueous solvent(s) in the liquid core, to raise the refractive index of the core above that of the containment tube, and this further limits utility.

The paper discussed immediately above also discussed the use of "Teflon AF" as an internal coating on a porous polyethylene hollow support fiber, the thickness of the coating being on the order of 1 μm. The resulting tube was filled with an acid-base indicator and reportedly responded to relatively high concentrations of ammonia gas (statically deployed in the vapor space over a 0.01 M solution of ammonia in a 50 mL capacity closed vessel) with a seemingly rapid response time (ca. 1 min). Coating the inside of a thin-walled porous fiber with the "AF" solution to produce an ultrathin layer of the latter polymer to produce a reliable or reproducible waveguide is not a commercially practical solution because, as is well known, "Teflon", including the AF variety, has very poor surface adhesion to most material unless special adhesion promoters are used (see, e.g., P. Dress and H. Franke, "A Cylindrical Liquid-Core Waveguide", Applied Physics, Part B, Volume 63, pages 12–19, 1996); and because such surface promoters can compromise the structural integrity of the porous tubing used as support. Also, it is impossible to produce uniform thicknesses of a polymer coating in the manner reported over any reasonable length of a tube and, especially, to produce such a coating in a reproducible manner from one batch to another. Further, such thin coatings cannot, on a practical basis, be produced without periodic occurrence of pinholes and this would make it impossible to use such tubing in in-vivo physiological applications or in any situation involving significant external pressure, e.g., for a situation in which a sensor is to be immersed in the depths of the ocean. In the latter case, the high collapsibility of supporting porous membrane tubes when pressure is applied from the outside will also compromise the structural integrity of such a sensor.

Importantly, the data provided by Hong and Burgess for the response speed of their "Teflon AF" coated tube teaches away from the use of a polymeric tube solely composed of "Teflon AF", rather than a bilayer structure involving a porous support structure and a "Teflon AF" adlayer. This is because the response time in the Hong-Burgess design is solely due to the permeation through the 1 μm thick "Teflon AF" layer, i.e, the transport in the support structure occurs through the free pore space in a microsecond time scale. The characteristic diffusion time of ammonia, a gas with a diffusion coefficient of 0.25 $cm^2$/s, through a 55 μm deep (see Hong and Burgess, page 78) air-filled pore is, however, only 120 msec. Accordingly, the ~1 min response time for a device having a 1 μm thick layer, as seen in FIG. 9 of Hong and Burgess, is actually not fast but very slow when the thickness is taken into account. It is well known that the characteristic time (loosely, response time for transport) for diffusive or permeative transport across a polymer wall varies directly with the square of the thickness of the polymer wall and inversely with the diffusion coefficient of the analyte of interest through the polymer. For a given analyte and polymer the diffusion coefficient remains constant and thus the response time increases with the square of the thickness (see, e.g., Dasgupta, P. K., "A Diffusion Scrubber for the Collection of Atmospheric Gases", Atmospheric Environment, Volume 18, pages 1593–1599, 1984). Hong and Burgess's own data on PTFE membranes (page 78) show the same behavior. The response time for ammonia decreases by a factor of ~4 as the membrane thickness is reduced by a factor of two (from 150 to 84 μm). Accordingly, if a polymer of ~1 μm thickness produces a response time ~1 min (and this for ammonia, a relatively low molecular weight, small, fast diffusing molecule), the response time for a 75 μm thick tube would be expected to be 5,625 minutes or close to 4 days, if one were to follow the teachings of Hong and Burgess. A "Teflon AF" tube having a wall thickness significantly less than 75 μm would not have sufficient rigidity to be employed as a sensor probe.

The above-discussed problems and deficiencies of the prior art are addressed and solved by the invention of the above-referenced related application. The techniques and apparatus which embody this solution are, nevertheless, susceptible to improvement. Specifically, enhancements in methodology, Particularly new applications thereof, and improvements in sensitivity and in the efficiency of collection of light which has interacted with the test specimen, have been desired.

SUMMARY OF THE INVENTION

The present invention comprises improvements in and to the analyses techniques of the above-referenced related application. The present invention thus encompasses new and novel applications of the unique technology of the related application and new and novel enhancements of the apparatus disclosed in the related application.

The present invention enhances the exploitation of two properties unique to a special kind of polymer membrane which has the following important properties: 1) the membrane structure is permeable to gases, vapors and certain chemical substances dissolved in a liquid matrix, 2) the membrane is comprised of a polymer material which is amorphous, optically clear and has a refractive index which is less than 1.33, and 3) the membrane can be formed into various self-supporting cylindrical shapes which, when filled with liquid, comprise an optical waveguide. The inside of the waveguide will be filled with a light conducting liquid. Also, any of a wide range of well known chemical solutions whose optical properties are modified when exposed to permeant gases or vapors can be dissolved in the waveguide filling fluid. In the practice of the invention to sense and measure chemical substances of interest, the exterior surface of the permeable waveguide is exposed to a controlled environment, i.e., the waveguide is disposed within a chamber, in which the substance(s) may be present in the gas or vapor phase or may be dissolved or dispersed in a liquid. Light is "shown", by various means, in the interior of the polymer waveguide. The light leaving the waveguide is then "measured". Light measuring techniques such as optical absorption (colorimetry), luminescence, fluorescence and Raman spectra can be used as modalities with which to characterize the substance(s) to be detected and measured.

The present invention thus employs the unique permeable liquid core waveguide of the related application wherein an appropriate light transmitting reagent forms the waveguide core. This permeable waveguide is fabricated from an optically clear amorphous polymer material having a lower refractive index than the flowing or stationary light transmitting reagent core liquid. A preferred material for use as the containment tube of a reagent core waveguide for practice of the invention is the copolymer of 2,2'-bis-trifluoromethyl-4,5 difluoro-1,3 dioxole (PDD) with tetrafluoroethylene (TFE) (TEFLON AF 2400). The reagent core liquid inside the waveguide is itself or contains a chemical indicator that will change its optical characteristics when the waveguide sensor is exposed to the analyte, the analyte diffusing through the highly permeable tube wall(s). The optical changes may, in accordance with the invention, be detected by one of the following techniques: UV/Vis absorption, fluorescence, chemiluminescence, or Raman spectrometry.

The sensitivity of a combined liquid core optical waveguide/gas or vapor sensor as described above is enhanced in accordance with the present invention. Particularly, the invention comprises improvements in the collection of emitted light and/or in the quantity of analyte to which the reagent is exposed per unit of time.

BRIEF DESCRIPTION OF THE DRAWINGS

The ability of those skilled in the art to understand the present invention, and to appreciate its numerous advantages, will be enhanced by reference to the accompanying figures in which.

DESCRIPTION OF DISCLOSED EMBODIMENTS

Figure 1:
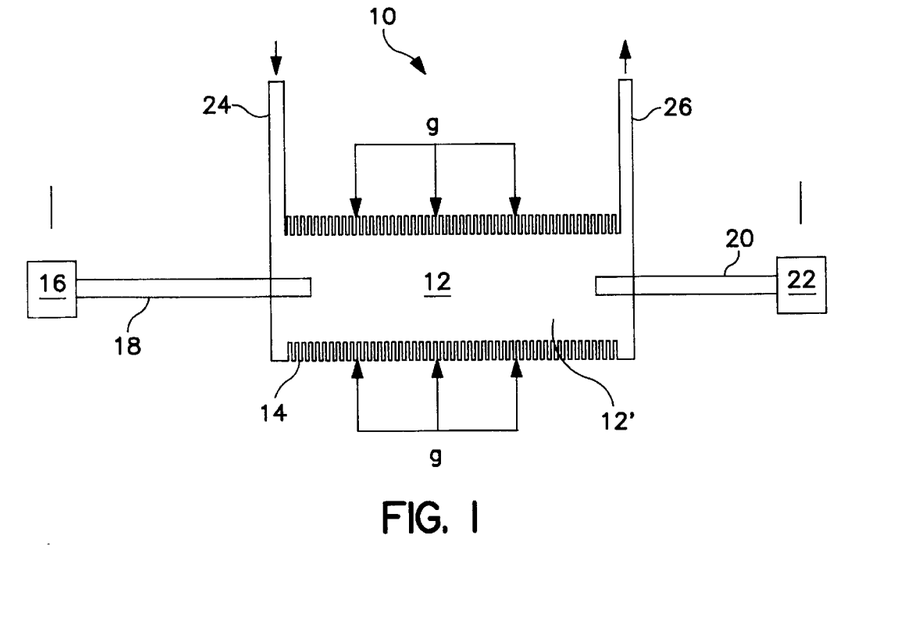
FIG. 1 is a schematic illustration of a flow-through sensor in accordance with the teachings of the related application.

The present invention employs a liquid core waveguide as the main body, i.e., the probe, of a sensor. Referring to FIG. 1, a liquid core waveguide having properties which enable its use in the invention is indicated generally at 10. Waveguide 10 comprises a substantially optically transparent liquid core region 12 surrounded by a material, i.e., a tube 14, having a lower refractive index (relevant to the wavelength range of light used) than the liquid material 12' comprising the core. Light will propagate inside the waveguide with negligible losses due to the total internal reflection at the surface of the lower refractive index material provided that the launching angle of the light into the core is within the acceptance angle of the material comprising tube 14.

In practice as schematically illustrated in FIG. 1, the sensor probe is coupled to a light source 16 which illuminates the core liquid 12' via a solid optical fiber 18, or bundle of such fibers. Light exits the waveguide at the end opposite to fiber 18 and is collected by an optical fiber(s) 20. Optical fiber(s) 20 deliver the collected light to an analysis instrument 22. FIG. 1 illustrates a "flow-through" technique in accordance with the related application wherein the core liquid 12, i.e., the indicator reagent, is delivered to the core region of the waveguide sensor via a supply conduit 24 and exits the core region via a discharge conduit 26. In a stationary, i.e., non-flowing, reagent embodiment, one of conduits 24 or 26 would be used to fill the core region of the waveguide with the reagent, after which the conduit would be capped, and the other conduit would be omitted.

The wall material of tube 14 must meet certain basic requirements. Firstly, it has to be permeable to the analyte and it must have a refractive index that is lower than that of the reagent, i.e., the core liquid 12'. Secondly, it must be optically clear. Thirdly, it must be relatively rigid so that, if the use dictates, the probe will be self-supporting. A preferred waveguide defining material is TEFLON AF 2400 which is the copolymer of PDD with TFE. It has recently been learned how to extrude PDD-TFE in the form of tubing having a wall thickness of 75 $\mu$m.

The tubing 14 has several important functions. Firstly, it forms a total reflection layer to entrap light injected via fiber 18 inside the tube so as to form a light waveguide. To form a liquid-core light waveguide, the tubing must define an outer layer with a refractive index which is lower than that of the liquid core. Since the copolymers of PDD with TFE have a refractive index in the range of 1.29 to 1.31, i.e., a refractive index which is lower than water and most organic solvents, almost any liquid can be used as the core liquid in a TEFLON AF 2400 tube. The waveguide action will significantly increase signal-to-noise ratio when compared to the prior art. This increase in sensitivity, in turn, allows the choice of a detection mode that will reduce the cost of detection. When UV/Vis absorption spectroscopy is used as the detection method, the waveguide action of the reagent-filled part of the sensor helps maintain high light throughput to the receiving fiber 20, making possible a long length and a large surface area for influx of the analyte, in the manner to be described below, into the sensor. In the absence of large light losses, the signal-to-noise ratio is linearly related to the amount of analyte transported into the sensor. Prior to the invention of the related application, the light pathlength of the sensor was typically only 1 mm long because of the inherent difficulty in keeping the light throughput for a longer path. In the practice of the present invention, a one meter long waveguide can be easily used, resulting in a signal-to-noise ratio improvement of three orders of magnitude over a sensor with 1-mm length, with a proportionate improvement in the limit of detection. When fluorescence, Raman, or chemiluminescence spectroscopy is used as the detection technique in instrument 22, the waveguide will enhance the signal by the integrating light signal, i.e., the additive effect which occurs along the waveguide. As will be obvious to those skilled in the art, when chemiluminescence is the detection modality, light injection via fiber 18 is not required.

The tubing 14 must also reduce interference caused by the effects of ambient light on the sensor. This result is accomplished because the optically clear, low refractive index tubing wall not only functions as a total reflection layer to keep the transmitted analysis light inside the waveguide, but it also substantially prevents ambient light from propagating through the lumen of the waveguide. Restated, any ambient light that is within the acceptance angle of the receiving fiber 20 will also be within the "total rejection angle" of the tubing 14. Therefore, although the tubing behaves like a mirror to internal light, it appears transparent to ambient light. Accordingly, ambient light is "rejected" while the internal guidance of analysis light and/or internally generated light is enhanced. A further reason for the relative immunity of the liquid-core guide sensor employed in the invention to the deleterious effects of ambient light is its high throughput of internal light which makes penetration of a fixed amount of ambient light less important.

The thin walled tube 14 must additionally function as an efficient analyte permeable membrane. Not only does the PDD-TFE copolymer display the lowest refractive index of any polymer, whereby it may function as a liquid core waveguide when filled with almost any clear liquid, it is also much more gas permeable than other fluoropolymers. Published data indicate that TEFLON AF 2400, for example, is 230 times more permeable to $CO_2$, $O_2$ and $H_2$ than polytetrafluoroethylene (PTFE). In the case of $CO_2$, the permeability of TEFLON AF 2400 to $CO_2$ is 3900 Barrer. Indeed, the permeability of PDD-TFE copolymers is comparable to that of polydimethylsiloxane (see, e.g., "Gas and Vapor Transport Properties of Amorphous Perfluorinated Copolymer Membranes Based on 2,2-bis trifluoromethyl-4, 5-difluoro-1,3-dioxole/tetrafluoroethylene", Pinnau and Toy, Journal of Membrane Science, Volume 109, pages 125–133, 1996). In FIG. 1, the migration of gas or vapor from the ambient environment to the core liquid through the permeable wall of tube 4 is indicated by "g".

The PDD-TFE tubing 14 also has sufficient rigidity to provide mechanical support for the associated components of the sensor. The analyte flux into the sensor is not only linearly dependent on available membrane area, it is also dependent inversely on the thickness of the membrane. Most gas permeable membrane tubes, because they have to be very thin to obtain sufficient flux, are lacking in rigidity and cannot be used as the structural support of the sensor. Thus, for a waveguide of any significant length, additional means of mechanical support would normally be necessary. The PDD-TFE copolymer displays high mechanical strength and rigidity. A narrow bore tube 14 with 75 $\mu$m thick walls is strong enough for most biological applications.

As noted above, the wall of polymeric tubing 14 provides containment for the reagent/core liquid 12'. Transport of the analyte through the tube wall, as noted, occurs by permeation. The process of permeation is governed by a combination of solubility in the polymer and diffusion through the polymer. For ionic constituents in a solution or other high molecular weight substances, the vapor pressure is very low and there is negligible loss of the internal constituents through the sensor wall.

The invention of the related application can be practiced in several modes. For example, the reagent inside the waveguide can be used in either a flowing or stationary manner. For a stable reagent that can be used in an equilibrium fashion, for example when sensing $pCO_2$ using a carbonate-bicarbonate buffer with an additional pH indicator, or when the sensor is to be disposable or where long term usability is not an important consideration, the indicator reagent can be permanently sealed inside the waveguide. Such non-flowing sensors will be stored inside a sealed package to prevent contamination of the reagent inside the waveguide from ambient air between fabrication and use. Where a stationary reagent core is used, the FIG. 1 sensor may be modified to permit the indicator reagent to be replaced or refurbished by including sealable liquid in/out caps, through which the waveguide can be filled with a fresh reagent, on one or both of conduits 24 and 26. For indicators that are chemically or photolytically unstable, the reagent will be continuously refreshed by using the waveguide essentially as a flow cell as represented by FIG. 1. For many applications, the optimum mode may be the use of a stationary liquid core for a desired measurement period, to cumulatively build the maximum analyte concentration possible, followed by flushing and recharging the core at the end of that measurement period to ready the sensor for a new measurement.

In yet another embodiment, the liquid core waveguide can be used in combination with another membrane that collects the analyte, followed by one or more sequential reagent additions and reactions. Those skilled in the art will perceive that plural analyte collection step could be sequentially carried out with the liquid core of the waveguide of FIG. 1 forming the final reaction zone.

A further mode of practice of the invention of the related application is to employ a solvent in which the gas specie of interest will dissolve in the core liquid of the permeable waveguide. Since the liquid core waveguide is a very sensitive detector, many permeated analytes can be detected directly by the spectral signature characteristic of the analyte gas itself, dissolved in a suitable liquid, without any reaction with an indicator reagent. For example, most of the volatile organic compounds have a strong absorbance band in the UV range. With a one meter long flow cell, such compounds can be detected at a concentration of 10 nanomolar. With the use of Raman spectroscopy as the detection mode, it is possible to differentiate between a variety of analytes and simultaneously measure them, although there will be some sacrifice in sensitivity relative to UV/Vis absorbance detection.

Figure 2:
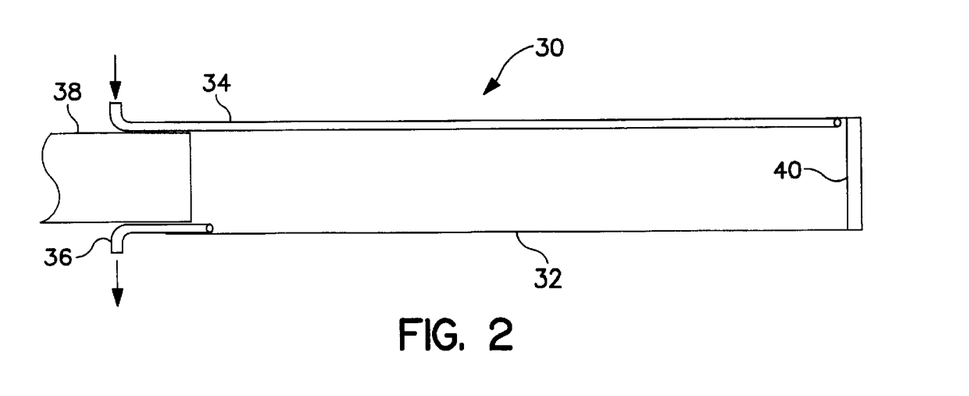
FIG. 2 is a schematic showing of a modified version of sensor of FIG. 1.

FIG. 2 depicts an alternative sensor probe in accordance with the invention of the related application. The sensor of FIG. 2 employs a gas and vapor permeable tube 32 as a liquid core optical waveguide 30. A suitable reagent is delivered into tube 32 via a conduit 34 which is arranged to have its discharge end located adjacent the distal end of waveguide 30. When the FIG. 2 sensor is operated in the flow-through mode, the reagent will exit waveguide 30 via a discharge conduit 36. Analysis light is launched into the proximal end of the waveguide core region via an optical fiber(s) 38. Light transmitted down the waveguide core is reflected at the distal end thereof by a mirror 40. Fiber(s) 38 thus function as both the analysis light launching and collection modality. The manner in which this is accomplished may, for example, be as explained in the description of FIG. 2 of U.S. Pat. No. 5,444,807. Obviously, the pathlength for the light in the sensor of FIG. 2 is essentially twice the length of tube 32.

The following are illustrative examples of practice of the invention of the related application.

$CO_2$ Detection: $CO_2$ may be sensed by filling the waveguide with an aqueous carbonate-bicarbonate buffer solution containing a pH indicator that undergoes a spectral change around the pH of such a buffer solution. Suitable pH indicators are phenol red and bromthymol blue. Visible absorption spectroscopy is used for sensing. The concentration of $CO_2$ outside the sensor (whether it is dissolved $CO_2$ in water or ambient $CO_2$ in the gas phase) quickly reaches equilibrium with $pCO_2$ (partial pressure of $CO_2$) inside the sensor. The pH inside the sensor and hence the exact spectrum of the indicator depends on the $pCO_2$ level. All general considerations relevant to any other fiber optic based $CO_2$ sensors will apply (see, e.g., DeGrandpre, above).

$O_2$ Detection: Oxygen may be sensed through utilization of both fluorometric and absorptiometric principles. Many fluorescent aromatic dye stuffs are known that are fluorescent and their fluorescence markedly decreases in the presence of oxygen due to Stern-Volmer Quenching. $O_2$ can be sensed using a solution of an oxygen-quenchable fluorescent dye inside the liquid waveguide. Inexpensive and highly sensitive absorptiometric oxygen sensing can be accomplished by filling the liquid core waveguide with a solution/suspension of leuco-methylene blue. This colorless dye substrate is readily oxidized by oxygen to form methylene blue which can be monitored by the emission from a red light emitting diode (LED). Other reagents such as ammoniacal cuprous chloride or chromous chloride (Chromium (II) chloride) which readily absorb oxygen to form highly colored products can also be used in the absorptiometric mode.

CO Detection: It is known that an alkaline solution of silver p-sulfoaminobenzoate or a solution of potassium tetrachloropaladate(II) readily absorbs CO and respectively form silver or palladium in a colloidal form that can be monitored by optical absorption measurement around 400 nm. Such solutions can be readily used for making a liquid core waveguide sensor for CO.

$H_2S$ Detection: Hydrogen sulfide is readily absorbed by an alkaline solution of sodium nitroprusside to from an intense purple color that can be monitored by emission from a green or yellow light emitting diode (LED) (see, e.g., "Nitroprusside and Methylene Blue Methods for Silicone Membrane Differentiated Flow-injection Determination of Sulfide in Water and Wastewater", Kuban et al, Analytical Chemistry, Volume 64, pages 36–43, 1992). This can form the basis of a highly sensitive and selective method for the measurement of $H_2S$ in ambient air and wastewater with an LED and a liquid core waveguide.

$NO_2$ Detection: Nitrogen Dioxide forms an intensely purple dye that can be monitored with a green LED upon reaction with Griess-Saltzman reagent (sulfanilic acid or sulfanilamide with 1-naphthylethylenediamine hydrochloride in a dilute acetic acid medium). Accordingly, by filling a liquid core waveguide with this reagent, $NO_2$ and/or nitrous acid may be selectively sensed. $NO_2$ can also be sensed in the lumionometric mode when a solution of luminol and sulfite is used in the waveguide, this reaction selectively producing chemiluminescence with luminol.

$NH_3$ Detection: High levels of ammonia can be monitored, employing the above-described principles of the $CO_2$ sensor, using an $NH_3$—$NH_4Cl$ buffer solution and an appropriate pH indicator and visible absorbance detection. Much lower levels of ammonia can be monitored using a system in which the ammonia is captured in a phenol-sodium nitroprusside solution followed by two sequential reactions, i.e., (a) with alkaline EDTA and then (b) with sodium hypochlorite. (see, e.g., "Electroosmotically Pumped Capillary Format Sequential Injection Analysis with a Membrane Sampling Interface for Gaseous Analytes", Liu and Dasgupta, Analytica Chimica Acta, Volume 308, pages 281–285, 1995). The color of the indophenol blue formed can be monitored with an orange-red LED emitting at 630 nm. An even more sensitive method consists also of a sequential reaction system and fluorometric sensing. In the latter technique, the ammonia is collected into an acidic receptor liquid and reacts with separately introduced solutions of o-phthalaldehyde and 2-mercaptoethanol (or sulfite) to form an intensely fluorescent isoindole.

Ozone Detection: Ozone can be detected either in the luminometric or the absorptiometric mode using the liquid-core waveguide. A great variety of intensely fluorescent dyes, including Eosin or Rhodamine, are oxidized by ozone and the oxidation is accompanied by light emission. Ozone also selectively decolorizes indigo derivatives and this bleaching can be monitored with a LED-based detector (see, e.g., "Automated Measurement of Aqueous Ozone Concentration", Darby et al, Process Control and Quality, volume 6, pages 229–243, 1995). Either sensing mode can be used for the monitoring of ozone in ambient air or for process control applications in ozonation plants for the production of potable water.

Hydrogen Peroxide Detection: Measurement of hydrogen peroxide has become important because it is the sterilizing agent of choice in many bioreactor operations. Hydrogen perioxide can be determined luminometrically using alkaline luminol containing a catalyst such as potassium ferricyanide in the core of the waveguide, this reagent produces intense chemiluminescence when contacted with $H_2O_2$. Hydrogen peroxide can also be monitored fluorometrically by using an oxidizable phenolic substrate such as p-Cresol and a peroxidase enzyme or its suitable mimic such as an ammoniacal solution of bovine hematin in the core of the waveguide. The resulting product is intensely fluorescent. Many calorimetric methods for measuring $H_2O_2$ are also known in the art.

Chlorine Detection: Chlorine is routinely monitored in water and air environments both in industry and by consumers. Chlorine reacts selectively with o-tolidine or tetramethylbenzidine in solution to form intensely yellow products that can be monitored by filling such a solution inside a liquid core waveguide and using a blue LED as the source for absorptiometric measurements.

Concentrated Acid Detection: The measurement of concentrated acids is an important problem in many industries. In the nuclear material processing industry, concentrated $HNO_3$ and HCl solutions are frequently used and it is important to measure the acidity in such media. This cannot be accomplished with simple pH sensing. Renewable reagent fiber optic based sensors have been used to address the problem using ion permeable membranes but there are difficulties due to the permeability dependence of such membranes on the presence of other membranes (see e.g., "A Renewable-Reagent Fiber-Optic Sensor for Measurement of High Acidities", Kuhn and Dyke, Analytical Chemistry, Volume 68, pages 2890–2894, 1996). Molecular $HNO_3$ and HCl can permeate through PDD-TFE and thus the use of a liquid core waveguide with a buffered indicator solution inside offers an ideal solution to this problem.

Detection of Organic Compounds in Water: The foregoing examples show that the analytes that can be detected/identified can be in the gas phase or the solution phase. Thus, the technology of the related application has applicability to the determination of dissolved organics in water whether these are present in trace amounts or in larger concentrations as occur in leakage of organic solvents or fuel from underground storage/disposal facilities into groundwater. In many cases, it will be possible to provide an organic solvent that is transparent in the near infrared (NIR) spectroscopy range or substantially into the UV range as the core of the waveguide which will collect the contaminants from water and on which direct NIR or UV spectroscopy can be carried out. In a second mode, specific reactions can be carried out with many organic compounds to yield products that are easily optically detectable. Intensely colored products are formed from halocarbons (contamination of ground water for example by chlorinated hydrocarbons is of considerable concern) by the Fujiwara reaction. A reaction based fiber optic sensor has already been reported for this purpose (see, e.g., "Multicomponent Determination of Chlorinated Hydrocarbons Using a Reaction-Based Chemical Sensor 1. Multivariate Calibration of Fujiwara Reaction Products", Henshaw et al, Analytical Chemistry, Volume 66, pages 3328–3334, 1994). The same reaction approach can be directly adapted to the present liquid core waveguide sensor with far greater sensitivity.

In the above discussion, it is implicit that laser and other light sources such as tungsten lamps, LEDs, mercury arc and others may be used as light sources for fluorescence and absorption measurement of the indicator fluid. A laser light source can be used in the present invention as means to generate Raman light spectra. Raman spectra have the particular advantage that molecules in the indicator fluid can exhibit unique "signature" spectra; thus enabling the separate analysis of specific molecules within a multi-molecular mixture in the fluid. The unique benefits of Raman spectroscopy within a liquid filled waveguide have been described in U.S. Pat. No. 5,604,587.

Figure 3:
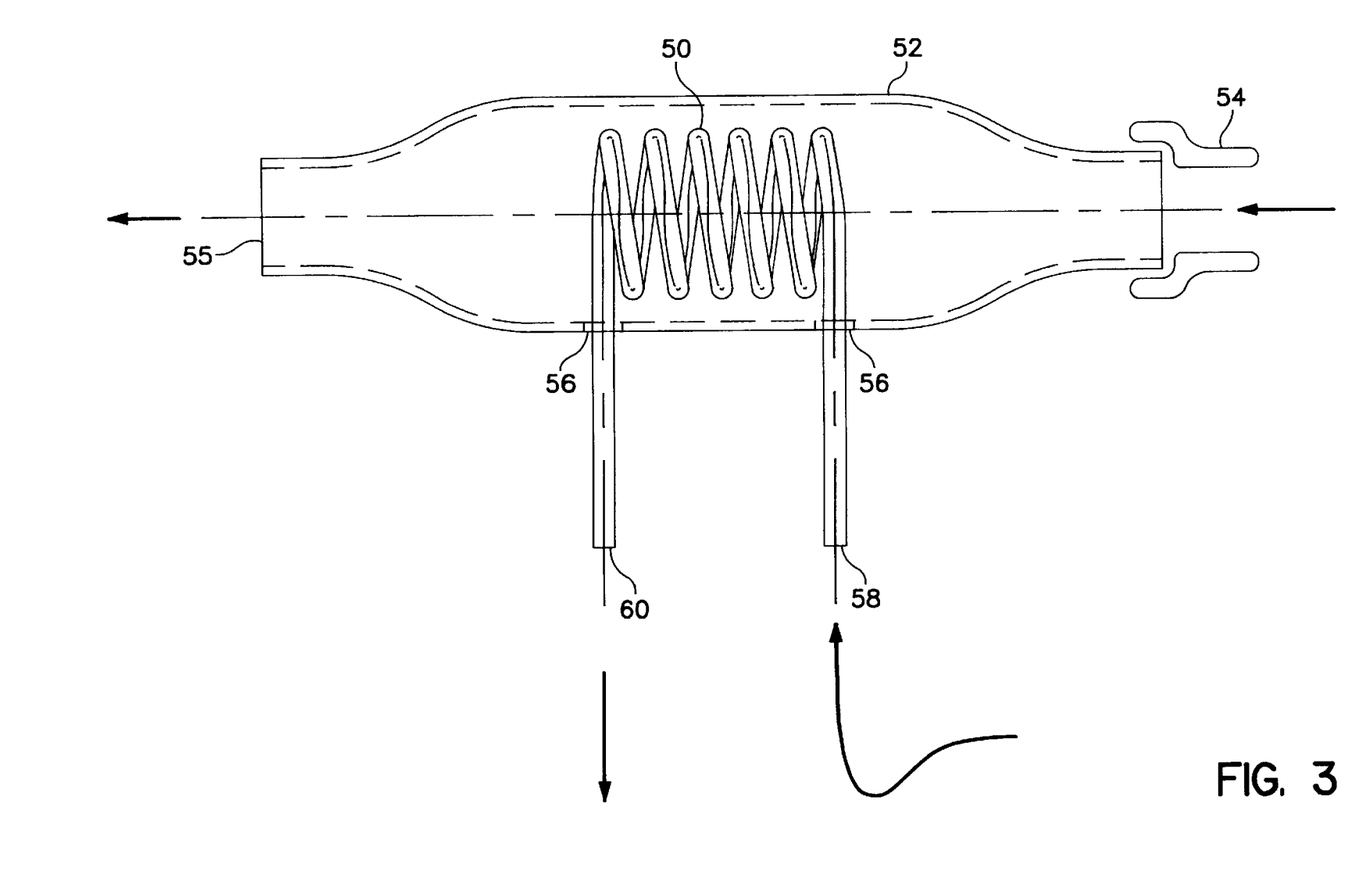
FIG. 3 schematically shows the practice of a sensing technique in accordance with the related application.

FIG. 3 discloses an embodiment of the present invention which employs a helical coil of permeable polymer tubing 50 mounted in a larger cylindrical housing 52 having a mouthpiece 54 at one end. A human subject will respire through the mouthpiece. His/her respiratory gases pass over the helical coil structure and exit via the opposite open end 55 of housing 52. The helical coiled shape of tubing 50 assures that a large length of the liquid reagent core waveguide formed thereby will be exposed to respired gases within the relatively small volume of the breath-through housing 52. The surface area of the permeable waveguide within the containment cylinder is thus maximized and, accordingly, the sensitivity of the probe that will be exposed to the transient gases of interest is also maximized. Additionally, as will be discussed further below in the description of FIG. 5, judicious selection of the internal volume of housing 52 and the size of the gas discharge opening 55 will further increase sensitivity by establishing a pressure differential across the tubing to thereby enhance the rate of gas permeation through the tube. The ends of the helical coil exit the housing 52 via small holes 56 which are sealed with an appropriate adhesive. Excitation light and core fluid are delivered to the proximal end 58 of the helical coil. The exit point for both the core fluid and the attenuated light signal is indicated at 60.

When the above-described novel sensing technique relies upon the detection of light generated by either fluorescence or chemiluminescence, the method and apparatus of the present invention provides a significant increase in sensitivity. Light generated by either fluorescence or chemiluminescence is scattered in all directions and, accordingly, only a small fraction of the total light generated is propagated along the interior of the liquid filled waveguide.

Figure 4A:
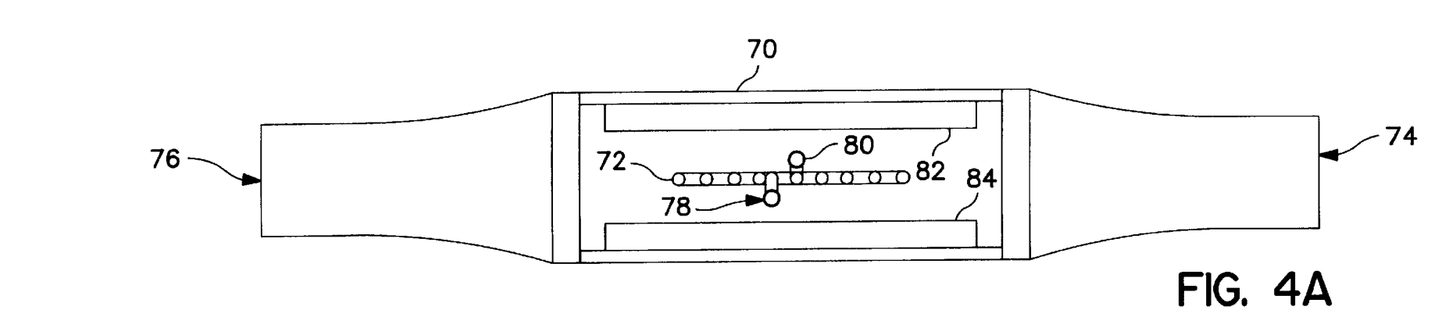
FIGS. 4A and 4B are respectively schematic top and side elevational views of improved apparatus in accordance with a first embodiment of the present invention.
Figure 4B:
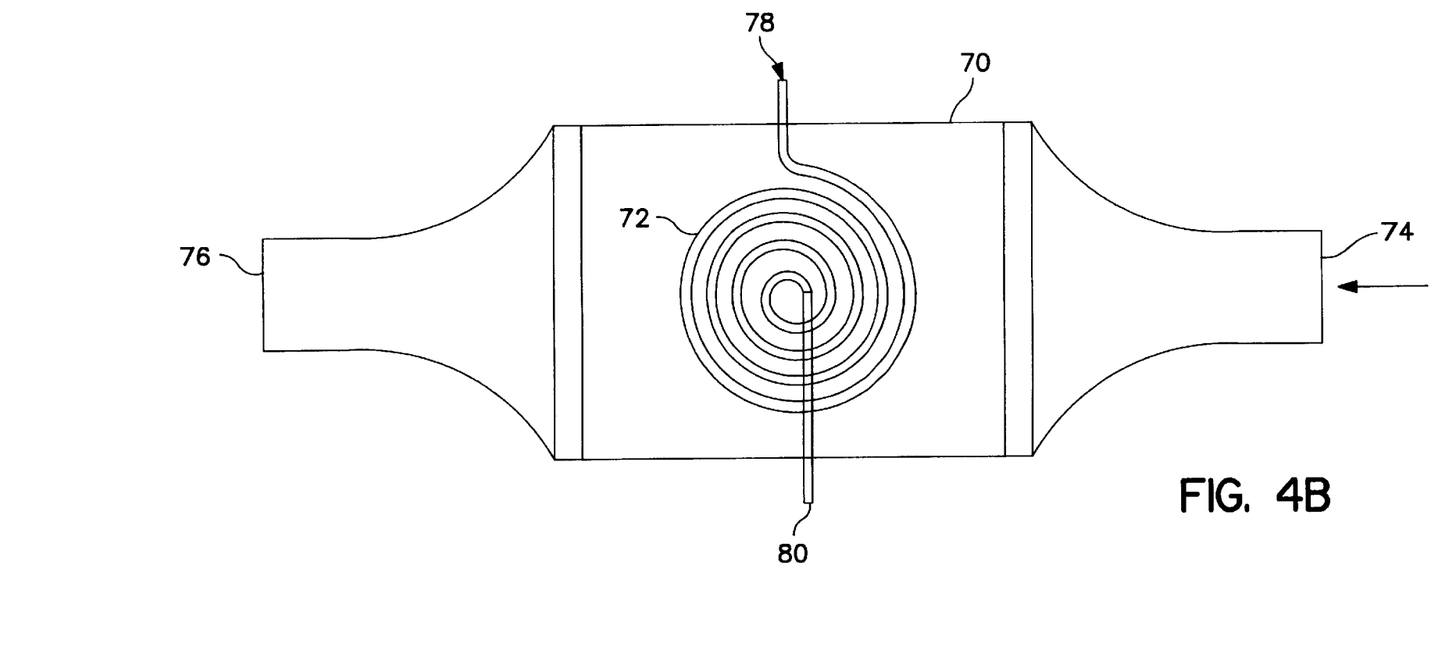

Referring to FIG. 4, a further embodiment of apparatus for use in the practice of the present invention comprises a vessel 70 in which a liquid core waveguide 72 is disposed. In this embodiment, the tubing comprising waveguide 72 is wound into a coil having the form of a flat spiral which essentially defines a plane. The flat spiral configuration of waveguide 72 compacts the length of the waveguide into a small volume. A specimen to be analyzed is introduced to vessel 70 at inlet port 74 and will exit the vessel at a discharge port 76. The reagent/core liquid will be introduced to waveguide 72 at inlet 78 and will be discharged from the waveguide at outlet 80. Considering the above-discussed example of an ozone detector, the reagent delivered to the waveguide via inlet 78 would be a fluorescent dye such as Eison or Rhodamine. The ozone containing gas will be introduced to vessel 70 via inlet port 74. Light will be emitted as a result of the stimulation, by injected light, of the product of oxidation of the dye by ozone which has permeated through the wall of waveguide 72. The emitted light will be efficiently detected by a pair of planar photocell arrays 82 and 84. Alternatively, one of the photocell arrays may be replaced with a flat mirror. The apparatus of FIG. 4 may, by additionally sensing light. transmitted through the waveguide, be employed for simultaneous absorption and fluorescent detection of independent gas species. When the FIG. 4 apparatus is employed to detect chemiluminescence, obviously a source of stimulation light is not required.

Figure 5:
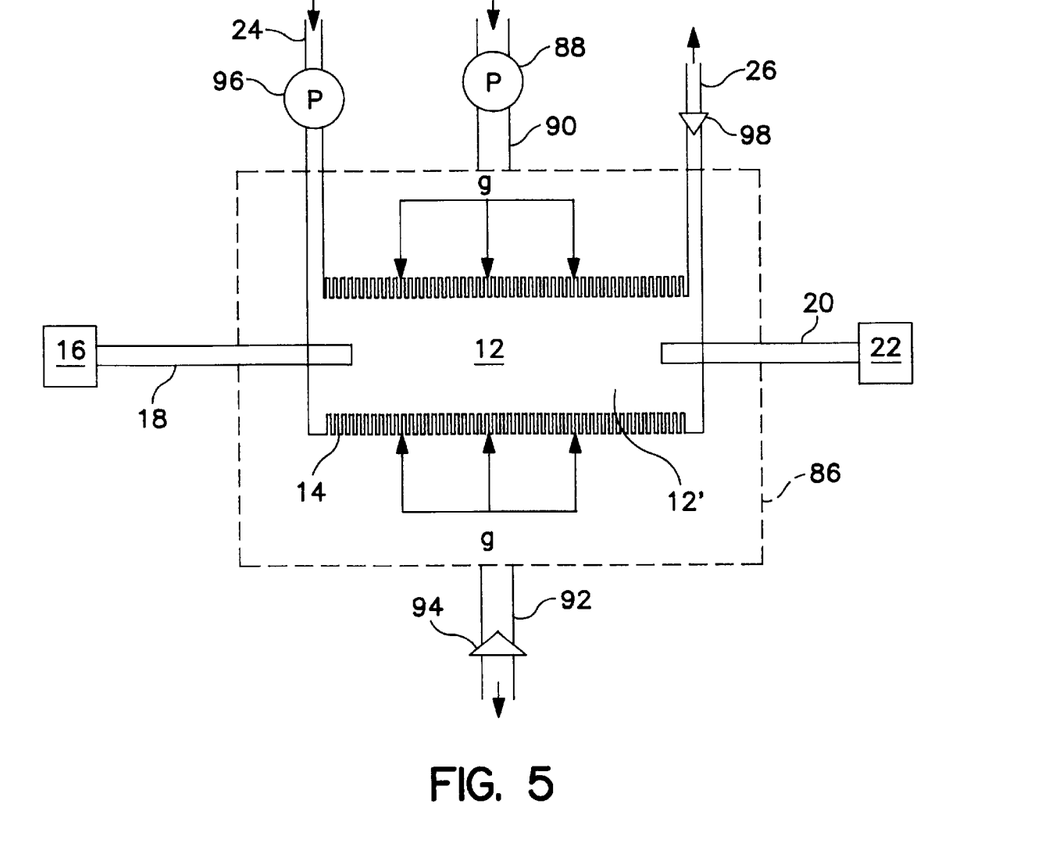
FIG. 5 schematically illustrates a second embodiment of the present invention, the apparatus of FIG. 5 being operable in an analysis or control process.

FIG. 5 schematically represents another way of enhancing the sensitivity of the techniques of the related application. As depicted in FIG. 5, the waveguide 10 of FIG. 1 is disposed within a housing 86 which may, in the manner to be described below, be pressurized. In the apparatus of FIG. 5, a specimen gas is delivered to the interior of container 86 by means of a pump 88 disposed in an inlet duct 90. The discharge conduit 92 for the specimen gas will be provided with a valve 94 which will be controllable. The pump 88 and valve 94 allows the pressure of the specimen gas about the exterior of the waveguide tube 14 to be controlled to a desired level above atmospheric pressure. This ability to increase the ambient pressure results in a very considerable increase in sensitivity by increasing the concentration of the specie of interest and, thereby, increasing the permeation of the gas specie through the wall of tube 14 through increasing the pressure gradient across the wall of tube 14.

Continuing to refer to FIG. 5, the disclosed embodiment of the invention may be employed as an in-line monitor for control purposes. For example, it may be desired to achieve control over the amount of a particular gas dissolved in a core liquid 12' which is pumped through tube 14 by means of a pump 96, the flow of the liquid 12' also being controlled by means of a valve 98. Through exercise of control over pumps 88 and 96 and valves 94 and 98, the pressure difference between the interior of housing 86 and the interior of tube 14 can be varied in such a manner as to cause gases to move into or out of the core liquid 12'. The detection modality, as described above in the discussion of FIG. 1, will then be employed to monitor and control the concentration of the gas of interest in the core liquid 12'.

While preferred embodiments have been described, various modifications and substitutions may be made thereto without departing from the spirit and scope of the invention. Accordingly, it is to be understood that the present invention has been described by way of illustration and not limitation.

What is claimed is:

1. A method for the optical detection of a chemical substance comprising the steps of:

filling the core region of a rigid tubular optical waveguide with a liquid which undergoes a change in an optical characteristic thereof upon exposure to a chemical substance of interest, the tubular waveguide being comprised of an optically clear amorphous polymer having a refractive index of less than 1.33, the liquid having an index of refraction which exceeds that of the waveguide, the waveguide being impermeable to the liquid delivered into the core region thereof and being permeable to gas and vapor;

exposing at least a portion of the exterior of the filled waveguide to an ambient environment which may include the chemical substance of interest;

controlling the pressure of the ambient environment to thereby influence the rate of permeation of the chemical substance of interest through the waveguide; and monitoring a change in an optical characteristic of the core liquid which occurs upon permeation of the chemical substance of interest through a wall of the tubular waveguide.

2. The method of claim 1 further comprising the step of:

transmitting analysis light into the liquid confined within the waveguide core region with a launching angle which is within the acceptance angle of the waveguide; and wherein the step of monitoring comprises:

receiving light which has passed through the core liquid and detecting a change in an optical characteristic of the core liquid by analyzing the received light.

3. The method of claim 2 wherein the step of controlling pressure comprises:

placing the waveguide within an enclosure, the interior of the enclosure defining the ambient environment; and varying the enclosure interior pressure to thereby vary the gradient between the waveguide core liquid pressure and the enclosure interior pressure.

4. The method of claim 3 wherein the step of varying pressure comprises:

exercising control over the enclosure interior pressure to establish a desired pressure in the enclosure.

5. The method of claim 4 wherein the step of placing the waveguide within an enclosure comprises:

placing the waveguide within a closed chamber, the chamber interior being isolated from the environment surrounding the enclosure.

6. The method of claim 3 wherein the step of placing the waveguide within an enclosure comprises:

positioning the waveguide within a breathing tube, the tube having a mouthpiece on a first end and a restricted discharge opening displaced from the mouthpiece, gas delivered to the tube interior via the mouthpiece flowing over the waveguide to reach the discharge opening.

7. The method of claim 3 wherein the step of monitoring comprises:

measuring the absorption of the transmitted analysis light by the liquid in the waveguide core region.

8. The method of claim 3 wherein the step of monitoring comprises:

measuring the fluorescence which occurs in the liquid in the waveguide core region.

9. The method of claim 3 wherein the step of monitoring comprises:

measuring the luminescence of the liquid in the waveguide core region.

10. The method of claim 3 wherein the step of monitoring comprises:

measuring the Raman spectra of the liquid in the core region of the waveguide.

11. The method of claim 3 further comprising:

forming a portion of the tubular waveguide into a spiral configuration prior to the filling thereof.

12. A method for the optical detection of chemical substances comprising:

forming a tubular member into a coiled configuration, the coiled member defining a first plane, said tubular member defining a hollow axial core region, said tubular member being comprised of an optically clear material which is gas and vapor permeable and liquid impervious, said material having a refractive index which is less than 1.33;

filling the core region of the tubular member with a light transmitting liquid reagent, said liquid undergoing a change in an optical characteristic thereof upon exposure to a chemical substance of interest which has diffused through said tubular member, said liquid having an index of refraction which exceeds that of said material comprising said tubular member;

placing the filled tubular member in an enclosure which includes the gaseous phase of a chemical substance which reacts with the reagent to produce light; and collecting light commensurate with the reaction on a least a first side of the tubular member in a plane which is substantially parallel to said first plane.

13. The method of claim 12 wherein the step of collecting comprises:

transmitting analysis light into the liquid confined within the waveguide core region with a launching angle which is within the acceptance angle of the waveguide; and receiving light emitted as a result of stimulation of the core liquid by the analysis light.

14. The method of claim 12 further comprising:

transmitting analysis light into the liquid confined within the waveguide core region with a launching angle which is within the acceptance angle of the waveguide;

receiving at one end of the waveguide analysis light which has passed through the core liquid; and detecting a change in the optical characteristics of the core liquid by analyzing the received analysis light.

15. The method of claim 12 further comprising:

increasing the enclosure interior pressure to thereby vary the gradient between the waveguide core liquid pressure and the enclosure interior pressure.

16. Apparatus for use in the optical detection of chemical species in the gas or vapor phase comprising:

a rigid tubular optical waveguide, said tubular waveguide being comprised of an optically clear amorphous polymer having a refractive index of less than 1.33, said tubular waveguide being impermeable to liquid and being permeable to gas and vapor;

a liquid reagent disposed in the core region of said tubular optical waveguide, said reagent having an index of refraction which exceeds the refractive index of said polymer, said reagent being light conducting and being characterized by an optical property which is modified when exposed to a chemical specie of interest in the gas or vapor phase;

an enclosure, said enclosure defining a chamber sized and shaped to receive at least a sensor portion of said optical waveguide, said enclosure having gas inlet and outlet ports whereby a pressurized specimen in gaseous form may be delivered into said chamber;

a light source coupled to a first end of said waveguide for transmitting analysis light into the reagent confined within the waveguide core region with a launching angle which is within the acceptance angle of the waveguide; and means for monitoring a change in an optical characteristic of the reagent which occurs upon permeation of the chemical specie of interest through the wall of the waveguide.

17. The apparatus of claim 16 wherein said enclosure includes means for causing the pressure of the specimen in the chamber to exceed the ambient pressure at the exterior of the enclosure.

18. The apparatus of claim 17 wherein said monitoring means comprises:
- a receiver positioned to detect light which is passed through the core liquid for a distance which is at least equal to the length of the waveguide.

19. The apparatus of claim 18 wherein said waveguide is formed into a coil to increase the surface area thereof disposed within said chamber.

20. The apparatus of claim 19 wherein said coiled waveguide is in the form of a flat spiral which defines a plane and wherein said monitoring means comprises:
- at least a first planar array of photocells, said array being disposed within said chamber and in substantially parallel relationship to said waveguide defined plane.

21. The apparatus of claim 17 wherein said waveguide is formed into a coil and wherein said enclosure comprises a breathing tube having a mouthpiece at a first end thereof.

* * * * *